(12) United States Patent
Love et al.

(10) Patent No.: US 9,949,642 B2
(45) Date of Patent: Apr. 24, 2018

(54) SYSTEMS, DEVICES, AND METHODS FOR MONITORING MEDICAL DEVICES

(71) Applicant: ABBOTT DIABETES CARE INC., Alameda, CA (US)

(72) Inventors: Michael R. Love, Pleasanton, CA (US); Jeffery M. Sicurello, Union City, CA (US); Gary Hayter, Oakland, CA (US); Xuandong Hua, Mountain View, CA (US); Mark Sloan, Redwood City, CA (US); John Dinh, San Leandro, CA (US); Glenn Berman, Alameda, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 15/154,862

(22) Filed: May 13, 2016

(65) Prior Publication Data

US 2016/0331232 A1 Nov. 17, 2016

Related U.S. Application Data

(60) Provisional application No. 62/161,794, filed on May 14, 2015.

(51) Int. Cl.
| | |
|---|---|
| *G08B 21/00* | (2006.01) |
| *A61B 5/00* | (2006.01) |
| *A61B 5/145* | (2006.01) |
| *G06F 19/00* | (2018.01) |

(52) U.S. Cl.
CPC ............ *A61B 5/002* (2013.01); *A61B 5/0004* (2013.01); *A61B 5/0022* (2013.01); *A61B 5/14532* (2013.01); *A61B 5/7225* (2013.01); *A61B 5/742* (2013.01); *G06F 19/3406* (2013.01)

(58) Field of Classification Search
None
See application file for complete search history.

(56) References Cited

U.S. PATENT DOCUMENTS

| | | |
|---|---|---|
| 7,620,438 B2 | 11/2009 | He |
| 7,826,382 B2 | 11/2010 | Sicurello et al. |
| 7,920,907 B2 | 4/2011 | McGarraugh et al. |
| 8,115,635 B2 | 2/2012 | Goodnow et al. |
| 8,223,021 B2 | 7/2012 | Goodnow et al. |
| 8,390,455 B2 | 3/2013 | Goodnow et al. |
| 8,543,183 B2 | 9/2013 | Peyser |
| 8,617,069 B2 | 12/2013 | Bernstein et al. |
| 8,734,344 B2 | 5/2014 | Taub |
| 8,880,137 B2 | 11/2014 | Say et al. |
| 9,000,929 B2 | 4/2015 | Hayter et al. |
| 9,008,743 B2 | 4/2015 | Hayter et al. |

(Continued)

OTHER PUBLICATIONS

WO, PCT/US2016/032548 ISR and Written Opinion, dated Aug. 26, 2016.

*Primary Examiner* — Brent Swarthout
(74) *Attorney, Agent, or Firm* — One LLP

(57) ABSTRACT

Systems, devices, and methods are provided that allow the monitoring of analyte levels within analyte monitoring systems. The analyte monitoring systems can be in vivo systems and can include a sensor control device with a sensor and accompanying circuitry, as well as a relay device for communicating with the sensor control device and a reader device.

12 Claims, 13 Drawing Sheets

(56) References Cited

U.S. PATENT DOCUMENTS

| | | |
|---|---|---|
| 9,336,423 B2 | 5/2016 | Goodnow et al. |
| 2003/0187338 A1 | 10/2003 | Say et al. |
| 2006/0001551 A1 | 1/2006 | Kraft et al. |
| 2008/0129486 A1 | 6/2008 | Jeckelmann et al. |
| 2008/0300476 A1 | 12/2008 | Stafford |
| 2009/0076359 A1 | 3/2009 | Peyser |
| 2009/0231125 A1 | 9/2009 | Baldus et al. |
| 2009/0240120 A1* | 9/2009 | Mensinger ............ A61B 5/7445 600/301 |
| 2010/0198034 A1 | 8/2010 | Thomas et al. |
| 2011/0213225 A1 | 9/2011 | Bernstein et al. |
| 2012/0157801 A1 | 6/2012 | Hoss et al. |
| 2014/0275898 A1 | 9/2014 | Taub et al. |
| 2014/0275907 A1 | 9/2014 | Feldman et al. |
| 2015/0182115 A1* | 7/2015 | DeHennis ............ G06F 19/3406 600/316 |
| 2016/0028821 A1* | 1/2016 | Petisce ................. A61B 5/0022 709/219 |

\* cited by examiner

SYSTEMS, DEVICES, AND METHODS FOR MONITORING MEDICAL DEVICES

CROSS-REFERENCE TO RELATED APPLICATIONS

This application claims priority to, and the benefit of, U.S. Provisional Patent Application 62/161,794 filed May 14, 2015, the contents of which are hereby incorporated by reference herein in its entirety and for all purposes.

FIELD

The subject matter described herein relates to systems, devices, and methods for continuous and on-demand monitoring of medical devices, for example, analyte monitoring devices.

BACKGROUND

The detection and/or monitoring of analyte levels, such as glucose, ketones, lactate, oxygen, hemoglobin A1C, or the like, can be vitally important to the health of an individual having diabetes. Diabetics generally monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost. For these and other reasons, needs exist for improved analyte monitoring systems, devices, and methods.

SUMMARY

Provided herein are a number of example embodiments directed to monitoring of medical devices in communication with other devices. Most of these embodiments are set forth in the context of an analyte monitoring environment but are not limited to such, and can be used with any two (or more) communicating devices in a medical environment or outside of a medical environment.

In many embodiments, a relay device is used to provide a communication link between a medical device, such as an analyte sensor control device, and a reader device, such as a mobile communication device or smartphone. The medical device can be placed in a continuous mode in which the medical device communicates with the relay device at a predetermined periodic time interval, or in an on-demand mode in which the medical device communicates with the relay device upon actuation by the user. In some embodiments, the relay device communicates with the medical device using a near field communication (NFC) communication protocol, and with the reader device using a Bluetooth protocol. In certain embodiments, the timing of the communication between the medical device and the relay device is synchronized to occur during idle time within the medical device.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1A:
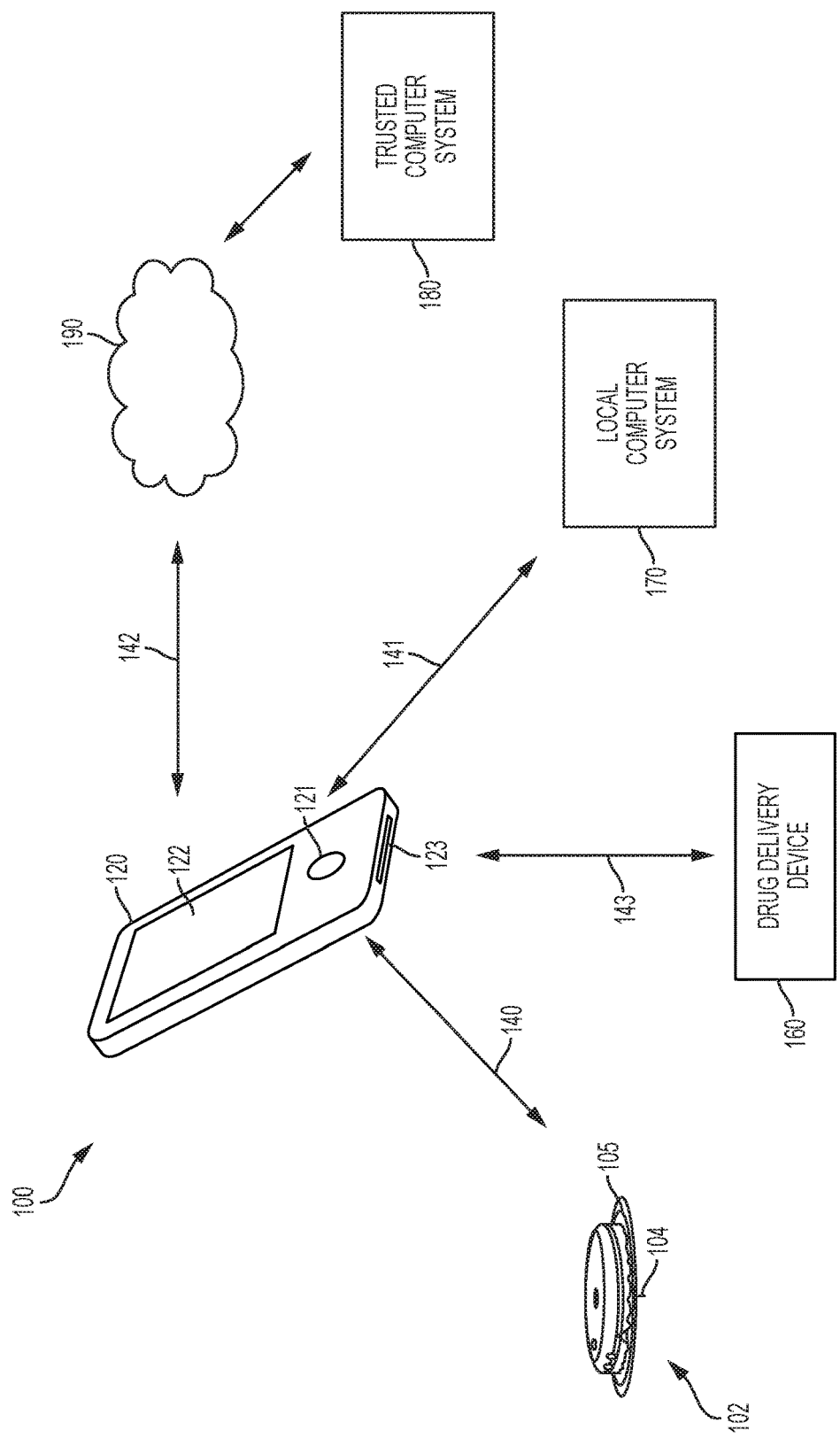
FIG. 1A is a high level diagram depicting an example embodiment of an analyte monitoring system for real time analyte (e.g., glucose) measurement, data acquisition and/or processing.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

A number of embodiments of systems, devices, and methods are provided that allow for monitoring of medical devices with other devices within an analyte monitoring environment. These embodiments can allow for a medical device, such as a sensor bearing device, to communicate with and be monitored by, for example, a relay device or adapter, which can in turn communicate with a reader device, such as a smart phone. Before describing these aspects of the embodiments in detail, however, it is desirable to describe examples of devices that can be present within these analyte monitoring environments.

Embodiments of Analyte Monitoring Systems

A number of systems have been developed for the automatic monitoring of the analyte(s) (like glucose, ketones, lactate, oxygen, hemoglobin A1C, or the like) in bodily fluid such as in the blood stream, in interstitial fluid ("ISF"), dermal fluid of the dermal layer, or in other biological fluid. Some of these systems are configured so that at least a portion of a sensor is positioned below a skin surface of a user, e.g., in a blood vessel, or in the dermal or subcutaneous tissue of the user, to obtain information about at least one analyte of the body.

As such, these systems can be referred to as "in vivo" monitoring systems. In vivo analyte monitoring systems include "Continuous Analyte Monitoring" systems (or "Continuous Glucose Monitoring" systems) that can broadcast data from a sensor control device to a reader device continuously without prompting, e.g., automatically according to a broadcast schedule. In vivo analyte monitoring systems also include "Flash Analyte Monitoring" systems (or "Flash Glucose Monitoring" systems or simply "Flash" systems) that can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

The in vivo analyte monitoring systems can be differentiated from "in vitro" systems that contact a biological sample outside of the body (or rather "ex vivo") and that typically include a meter device that has a port for receiving an analyte test strip carrying bodily fluid of the user, which can be analyzed to determine the user's blood sugar level. While in many of the present embodiments the monitoring is accomplished in vivo, the embodiments disclosed herein can be used with in vivo analyte monitoring systems that incorporate in vitro capability, as well has purely in vitro or ex vivo analyte monitoring systems.

The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. Other devices such as personal computers have also been utilized with or incorporated into in vivo and in vitro monitoring systems.

FIG. 1 is an illustrative view depicting an example in vivo analyte monitoring system 100 with which all of the embodiments described herein can be used. System 100 can have a sensor control device 102 and a reader device 120 that communicate with each other over a local communication path (or link) 140, which can be wired or wireless, and unidirectional or bidirectional. In embodiments where path 140 is wireless, any near field communication (NFC) protocol, RFID protocol, Bluetooth or Bluetooth Low Energy protocol, Wi-Fi protocol, proprietary protocol, or the like can be used, including those communication protocols in existence as of the date of this filing or their later developed variants.

Bluetooth (BT) is a well-known standardized short range wireless communication protocol, and Bluetooth Low Energy is a version of the same that requires less power to operate. Bluetooth Low Energy (Bluetooth LE, BTLE, BLE) is also referred to as Bluetooth Smart or Bluetooth Smart Ready. A version of BTLE is described in the Bluetooth Specification, version 4.0, published Jun. 30, 2010, which is explicitly incorporated by reference herein for all purposes. Bluetooth and BTLE operate in the same frequency band (2.4 GHz-2.24835 GHz). Bluetooth uses an adaptive frequency hopping technique sometimes referred to as frequency-hopping spread spectrum that can, in many embodiments, hop between use 79 one MHz channels. BTLE uses digital modulation techniques or direct-sequence spread spectrum and can, in many embodiments, hop between 40 two MHz channels. In light of the present description, those of ordinary skill in the art will readily understand the subject matter referred to by the terms "Bluetooth" and "Bluetooth Low Energy" and their respective acronyms (BT, BTLE, BLE, etc.).

The term "NFC" applies to a number of protocols (or standards) that set forth operating parameters, modulation schemes, coding, transfer speeds, frame format, and command definitions for NFC devices. The following is a non-exhaustive list of examples of these protocols, each of which (along with all of its sub-parts) is incorporated by reference herein in its entirety for all purposes: ECMA-340, ECMA-352, ISO/IEC 14443, ISO/IEC 15693, ISO/IEC 18000-3, ISO/IEC 18092, and ISO/IEC 21481. In light of the present description, those of ordinary skill in the art will readily understand the subject matter referred to by the term "near field communication" and its acronym NFC.

Reader device 120 is also capable of wired, wireless, or combined communication, either bidirectional or unidirectional, with either or all of: a drug delivery device 160 over communication path (or link) 143, a local computer system 170 over communication path (or link) 141, and with a network 190 over communication path (or link) 142. The same wireless protocols described for link 140 can likewise be used for all or part of links 141, 142, and 143.

Reader device 120 can communicate with any number of entities through network 190, which can be part of a telecommunications network, such as a Wi-Fi network, a local area network (LAN), a wide area network (WAN), the internet, or other data network for unidirectional or bidirectional communication. A trusted computer system 180 can be accessed through network 190. In an alternative embodiment, communication paths 141 and 142 can be the same path. All communications over paths 140, 141, 142, and 143 can be encrypted and sensor control device 102, reader device 120, remote computer system 170, and trusted computer system 180 can each be configured to encrypt and decrypt those communications sent and received.

Variants of devices 102 and 120, as well as other components of an in vivo-based analyte monitoring system that are suitable for use with the system, device, and method embodiments set forth herein, are described in US Patent Application Publ. No. 2011/0213225 (the '225 Publication), which is incorporated by reference herein in its entirety for all purposes.

Sensor control device 102 can include a housing 103 containing in vivo analyte monitoring circuitry and a power source. The in vivo analyte monitoring circuitry can be electrically coupled with an analyte sensor 104 that can extend through an adhesive patch 105 and project away from housing 103. Adhesive patch 105 contains an adhesive layer (not shown) for attachment to a skin surface of the body of the user. (Other forms of body attachment to the body may be used, in addition to or instead of adhesive.)

Sensor 104 is adapted to be at least partially inserted into the body of the user, where it can make fluid contact with that user's body fluid (e.g., interstitial fluid (ISF), dermal fluid, or blood) and be used, along with the in vivo analyte monitoring circuitry, to measure analyte-related data of the user. Generally, sensor control device 102 and its components can be applied to the body with a mechanical applicator or inserter in one or more steps, as described in the incorporated '225 Publication, or in any other desired manner.

After activation, sensor control device 102 can wirelessly communicate the collected analyte data (such as, for example, data corresponding to monitored analyte level and/or monitored temperature data, and/or stored historical analyte related data) to reader device 120 where, in certain embodiments, it can be algorithmically processed into data representative of the analyte level of the user and then displayed to the user and/or otherwise incorporated into a diabetes monitoring regime. In many of the embodiments described herein, the communication from sensor control device 102 to reader device 120 occurs through a relay device, to be described in more detail in the subsequent section.

Reader device 120 includes a display 122 to output information to the user and/or to accept an input from the user (e.g., if configured as a touch screen), and one or more optional user interface components 121, such as a button, actuator, touch sensitive switch, capacitive switch, pressure sensitive switch, jog wheel or the like. Reader device 120 can also include one or more data communication ports 123 for wired data communication with external devices such as computer system 170. Reader device 120 may also include an integrated or attachable in vitro meter, including an in vitro test strip port (not shown) to receive an in vitro analyte test strip for performing in vitro blood analyte measurements.

Sensor control device 102 and/or reader device 120 can each be configured to communication with a drug delivery device 160 that is capable of injecting or infusing a drug, such as but not limited to insulin, into the body of the individual wearing sensor control device 102. Like reader device 120, drug delivery device 160 can include processing circuitry, non-transitory memory containing instructions executable by the processing circuitry, wireless or wired communication circuitry, and a user interface including one or more of a display, touchscreen, keyboard, an input button or instrument, and the like. Drug delivery device 160 can include a drug reservoir, a pump, an infusion tube, and an infusion cannula configured for at least partial implantation into the user's body. The pump can deliver insulin from the reservoir, through the tube, and then through the cannula into the user's body. Drug delivery device 160 can include instructions, executable by the processor, to control the pump and the amount of insulin delivered. These instructions can also cause calculation of insulin delivery amounts and durations (e.g., a bolus infusion and/or a basal infusion profile) based on analyte level measurements obtained directly or indirectly from sensor control device 102. The instructions can start drug delivery, stop drug delivery, increase or decrease the drug dosage, or modify a basal profile or a bolus dosage administered to the user. Embodiments of system 100 that include a drug delivery device 160 can be configured to operate as a semi-closed loop system or a fully closed loop system (sometimes referred to as an artificial pancreas).

Sensor control device 102, reader device 120, and drug delivery device 160 can each be configured to communicate with a local or remote computer system 170 (such as a personal or laptop computer, a tablet, or other suitable data processing device), a remote trusted computer system 180 (which can include one or more computers, servers, networks, databases, and the like), and/or a communication network 190 (e.g., the internet).

Computer system 170 may be a personal or laptop computer, a tablet, or other suitable data processing device. Computer 170 can be either local (e.g., accessible via a direct wired connection such as a universal serial bus (USB) connection) or remote to reader device 120 and can be (or include) software for data management and analysis and communication with the components in analyte monitoring system 100. Operation and use of computer 170 is further described in the '255 Publication incorporated herein. Analyte monitoring system 100 can also be configured to operate with a data processing module (not shown), also as described in the incorporated '225 Publication.

Trusted computer system 180 can be used to perform authentication of sensor control device 102 and/or reader device 120, used to store confidential data received from devices 102 and/or 120, used to output confidential data to devices 102 and/or 120, or otherwise. Trusted computer system 180 can include one or more computers, servers, networks, databases, and the like. Trusted computer system 180 can be within the possession of the manufacturer or distributor of sensor control device 102, either physically or virtually through a secured connection, or can be maintained and operated by a different party (e.g., a third party). Trusted computer system 180 can be trusted in the sense that system 100 can assume that system 180 provides authentic data or information. Trusted computer system 180 can be trusted simply by virtue of it being within the possession or control of the manufacturer, e.g., like a typical web server. Alternatively, trusted computer system 180 can be implemented in a more secure fashion such as by requiring additional password, encryption, firewall, or other internet access security enhancements that further guard against counterfeiter attacks or attacks by computer hackers.

The processing of data and the execution of software within system 100 can be performed by one or more processors of reader device 120, relay device 200 (described below), computer system 170, and/or sensor control device 102. For example, raw data measured by sensor 104 can be algorithmically processed into a value that represents the analyte level and that is readily suitable for display to the user, and this can occur in sensor control device 102, reader device 120, or computer system 170. This and any other information derived from the raw data can be displayed in any of the manners described above (with respect to display 122) on any display residing on any of sensor control device 102, reader device 120, or computer system 170. The information may be utilized by the user to determine any necessary corrective actions to ensure the analyte level remains within an acceptable and/or clinically safe range.

Embodiments of Relay Devices

The embodiments of analyte monitoring system 100 described herein can also include a relay device 200 configured to act as an intermediary and facilitate communication between two or more devices of system 100. For example, if two devices of system 100 cannot communicate directly with each other because they are not configured to communicate according to a common communication protocol, then relay device 200 can be used. In such cases, relay device 200 is capable of communicating directly with each of the two devices according to their respective communication protocols, passing the information from one device to the other.

Figure 1B:
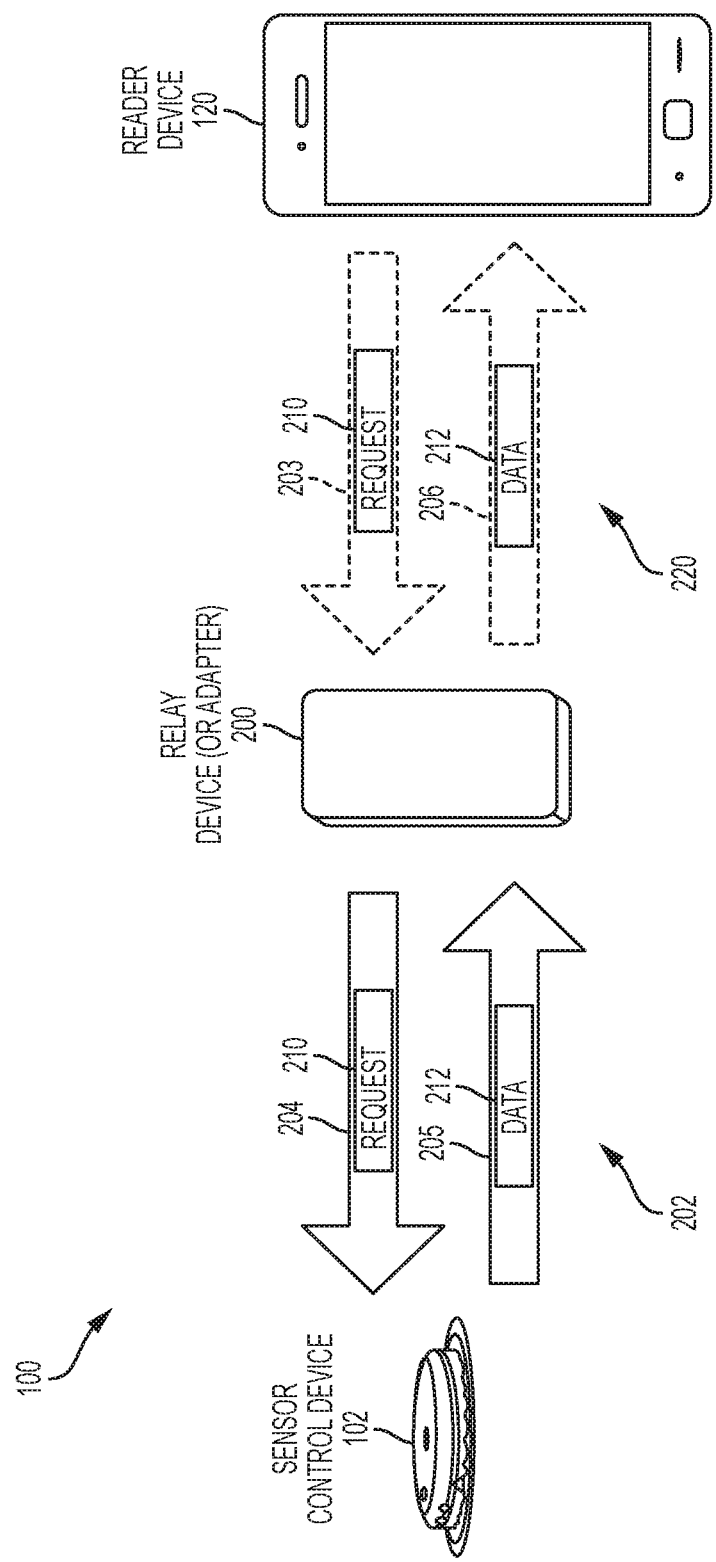
FIG. 1B is a block diagram depicting an example embodiment of an analyte monitoring system with a relay device.

Such a situation is described with respect to the example embodiment depicted in the block diagram of FIG. 1B. Here, it is desirable for sensor control device 102 and reader device 120 to be able to wirelessly communicate with each other; however, sensor control device 102 and reader device 120, in this situation, are not capable of communicating with the same protocol. For example, sensor control device 102 may only have the ability to communicate according to an NFC protocol, while reader device 102 does not have NFC communication capability (e.g., as in certain smartphones) and must communicate according to a different protocol, such as Bluetooth or Bluetooth Low Energy.

In order to permit communication between sensor control device 102 and reader device 120, relay device 200 (or adapter device 200) is used as an intermediary. Relay device 200 is capable of communicating directly with sensor control device 102 according to a first protocol (e.g., NFC) over communication link 202, and relay device 200 is capable of communicating directly with reader device 120 according to a different, second protocol (e.g., BT or BTLE) over communication link 220.

Communication links 202 and 220 can both be bidirectional links as shown in FIG. 1B. Links 202 and 220 can also be unidirectional links (in the same upstream or downstream direction) or one link 202 or 220 can be bidirectional while the other is unidirectional. In many embodiments, communication links 202 and 220 are wireless links, although in some embodiments one or both of links 202 and 203 can be wired or wireline links. In many embodiments, system 100 is configured such that sensor control device 102 and relay device 200 communicate with each other directly, i.e., with no other intermediaries (e.g., other relays or networks) between them. Likewise, in many embodiments reader device 120 and relay device 200 also communicate directly with each other.

Any communication protocol (including all protocols described herein) can be used for links 202 and 220. In many embodiments the protocols are different and relay device 200 acts as an adapter, e.g., adapting one device to operate with another. However in some embodiments the protocols are the same, in which case relay device 200 repeats a received message or transfers it from one established link to another (e.g., between BT pairings) without an adaption function such as to increase the communication range between sensor control device 102 and reader device 120.

Although communication link 220 has thus far been described as existing between relay device 200 and reader device 120, link 220 can be between relay device 200 and any other desired device. For example, in some embodiments link 220 exists between relay device 200 and drug delivery device 160 such that those two devices can communicate directly.

The embodiment of FIG. 1B is described with respect to an example process where reader device 120 wirelessly transmits or sends a request 210 that, when read by sensor control device 102, is interpreted as a request for data that is indicative of a current analyte level and/or one or more previous or historical analytes to be sent or reported from sensor control device 102 back to reader device 120 via relay device 200. Of course, as described herein, communication routines for other purposes are contemplated as well.

In this embodiment, reader device 120 can be a smartphone having one or more instructions stored in memory (e.g., an installed local program, or downloaded application or "app") that, when executed by processing circuitry, provide a user interface for controlling communication with sensor control device 102 through relay device 200. For example, a downloaded "app" can cause the sending of instructions that place sensor control device 102 into continuous mode in which sensor control device 102 obtains measurements of the analyte level at a time interval determined by the user. The app can also include programming to provide alarms if the analyte level is outside a predetermined range or reader device 120 is out of communication range with relay device 200, graphic representations of monitored analyte levels, battery charge levels of the relay device and sensor control device, and wireless signal strength, to name a few.

In the embodiment of FIG. 1B, reader device 120 can wirelessly send a transmission 203 containing request 210 to relay device 200 over link 220 according to a BT or BTLE protocol. This transmission can occur after a paired relationship is established between device 120 and 200 according to the BT or BTLE protocols. Request 210 itself can have varying degrees of complexity, such as a bit or several bits set in a particular location to indicate that the transmission is a request for data, to more complex data arrangements. Request 210, for example, can be contained within a payload or data portion of a packetized transmission, or request 210 can be within a header to the packetized transmission.

After receiving transmission 203 formatted according to the BT or BTLE protocol, relay device 200 is adapted, either through hardware, software, or a combination of the two, to transfer request 210 to a suitable format for inclusion in transmission 204 sent from relay device 200 to sensor control device 102 according to an NFC protocol. This process, performed by relay device 200, of taking a first transmission received according to one protocol, extracting and/or reading the relevant portion of the transmission, and then preparing a second transmission, to be sent according to a second (different) protocol, that contains the relevant portion or otherwise conveys the same message as the received first transmission, is referred to herein as the "transfer process" of relay device 200.

In some embodiments, the transfer process can include demodulating transmission 203, decoding the demodulated information, reading the decoded information, and then storing the relevant portion, in this case request 210, at least temporarily in the memory of relay device 200. Request 210 can be inserted into a data payload portion in the new transmission 204, or transmission 204 can be formatted to communicate the same message conveyed by request 210 using, for example, an altogether different sequence of data. Transmission 204 is then sent to sensor control device 102. Transmission 204 can be continually sent for a given or predetermined time period until a response is received from sensor control device 102. In some embodiments encryption can be applied in the communication process as desired, and relay device 200 can be configured to decrypt and re-encrypt communications to be transferred.

In some embodiments, reader device 120 does not send request 210 to relay device 200, but instead sends an instruction within transmission 203 that instructs relay device 200 to generate its own transmission that is interpretable by sensor control device 102 as a scan request. When relay device 200 is placed into close proximity with sensor control device 102, if it is not already in close proximity, then upon entering into communication range, relay device 120 can successfully send transmission 204 to sensor control device 102 without performing any transfer process with respect to request data or other data received from reader device 120.

After receiving transmission 204, sensor control device 102 can perform any required demodulation, decoding, and/or decrypting, and read or interpret request 210. If necessary, sensor control device 102 can take an analyte measurement of the user. A new transmission 205 is created and sent by sensor control device 102 with the requested data 212 (e.g., current and/or historical analyte levels) included within. In some embodiments, transmission 205 is a passive NFC transmission generated and sent with energy harvested from the received transmission 204.

After receiving transmission 205, relay device 200 can then demodulate and decode transmission 205 as necessary, extract data 212, and store it at least temporarily in memory. Relay device 200 can create and send a new transmission 206, with data 212 contained therein, to reader device 120. In many embodiments data 212 can be passed through by relay device without any modification or alteration to the information conveyed by the received analyte data. Such can be accomplished while still reformatting (including, e.g., packetizing, compressing and/or encrypting) the received data for transmission according to the different communication protocol, e.g., BT or BTLE. In other embodiments data 212 can be processed or modified if desired. For example, data 212 can be compressed or reformatted prior to insertion within transmission 206. In some embodiments, if data 212 is in a raw format, then algorithmic processing can be performed on data 212 to convert data 212 into a state that more readily conveys the analyte level of the user.

After receiving transmission 206, reader device 120 can demodulate and decode it, and extract data 212. If data 212 is in a relatively raw format, then reader device 120 can process the data algorithmically to convert it into a format that more readily conveys the user's analyte level. The analyte data can then be displayed on display 122 of reader device 120 or transferred to and utilized by the other devices in system 100.

Figure 2:
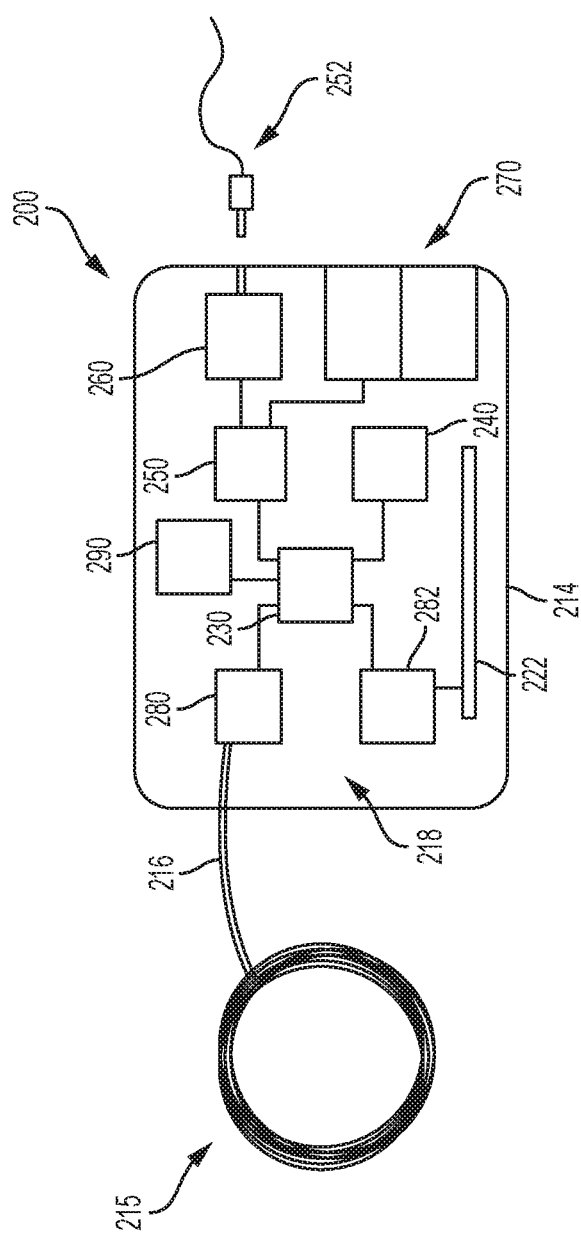
FIG. 2 is a block diagram depicting an example embodiment of a relay device.

FIG. 2 is a block diagram depicting an example embodiment of relay device 200. Here, relay device 200 includes circuitry 218 for communicating with sensor control device 102 and reader device 120, and for processing received data and instructions. Circuitry 218 can be implemented as one or more integrated circuit (IC) packages coupled with a printed circuit board (PCB). The various functional components shown in FIG. 2 can each be implemented as a discrete IC package connected together via traces in the PCB or buses disposed on the PCB, or the functional components can be combined into a single IC package (e.g., with a single chip or as a multi-chip module (MCM) and the like).

Communication circuitry 280 is configured to accomplish wireless communication with sensor control device 102. Electronically coupled to communication circuitry 280 is antenna 215 for sending and receiving commands, responses, and other information to and from sensor control device 102. Relay device circuitry 218 can further include communication circuitry 282 or other electronics for wirelessly communicating with reader device 120. Electronically coupled to communication circuitry 282 is an antenna 222 for sending and receiving commands and responses associated with reader device 120.

Communication circuitry 280 and 282 can include one or more transmitters, receivers, transceivers, encoders, decoders, processors, and memories to enable control and performance of communication routines.

Some examples of commands include commands for device authentication, commands for setting sensor control device 102 into continuous mode, requests for analyte readings, date and time, and the like. Responses can include, for example, analyte readings or data, date and time of the readings, temperature data, calibration data, authentication data, sensor identification information, battery state of sensor control device 102, and others.

One or both antennas 215 and 222 can be internal to housing 214 enclosing relay device circuitry 218 or can be external to housing 214. For example, in FIG. 2, antenna 215 is external to housing 214 while antenna 222 is internal to housing 214. External antennas can be physically and electronically coupled to relay device circuitry 218 by one or more wire cables 816. Antennas 215, 222 are typical antennas used with the wireless protocols being employed. In some embodiments, antennas 215, 222 can be flex circuits of conductive tracings on flexible materials. In other embodiments, antennas 215, 222 can be conductive tracings on a thin PCB, or alternatively can be conductive tracings on the PCB that includes the relay device circuitry 218. In FIG. 2 antenna 215 is depicted as a loop antenna for an NFC link and antenna 222 is depicted as a dipole antenna for BT or BTLE.

As described above, any communication protocol, such as an NFC protocol, RFID protocol, Bluetooth (BT) or Bluetooth Low Energy (BTLE, BLE) protocol, Wi-Fi protocol, proprietary protocol, or the like, including those communication protocols in existence as of the date of this filing or their later developed variants, can be the basis for communication controlled and performed by communication circuitry 280 and 282. In some embodiments, communication circuitry 280 operates according to an NFC protocol and communication circuitry 282 operates according to a BT or BTLE protocol. In yet other embodiments, relay device 200 can electronically communicate with reader device 120 and/or or sensor control device 102, through a wire connection.

As already mentioned, because relay device 200 is coupled, wirelessly or electronically, to both reader device 120 and sensor control device 102, relay device 200 can pass communications from reader device 120 to sensor control device 102 and from sensor control device 102 to reader device 120.

Referring still to FIG. 2, relay device 200 can include one or more processors 230, which can be implemented in any desired fashion, such as by multiple dedicated microprocessor chips, or as processing circuitry distributed throughout various functional portions of relay device 200. Processor 230 can be programmed to execute instructions related to communicating with sensor control device 102 and reader device 120. Processor 230 can also be programmed to obtain, store, and transfer data readings from sensor control device 102 to reader device 120. As will be described later, processor 230 additionally be can programmed to synchronize the timing of when sensor control device readings are transferred to relay device 200.

Figure 3A:
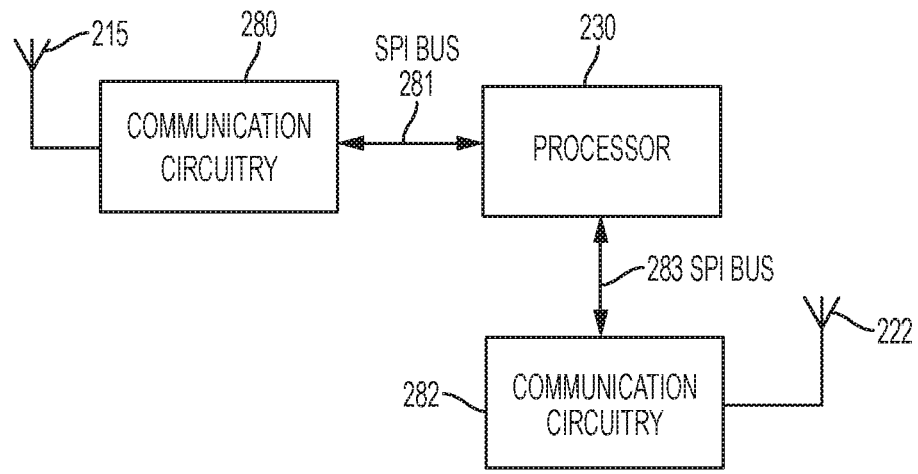
FIGS. 3A-B are block diagrams depicting example embodiments of portions of a relay device.

Communication circuitry 280 and 282 can each be connected with processor 230. In some embodiments, the connection can be accomplished serially, such as with serial peripheral interface (SPI) buses 281 and 283 as depicted in the block diagram of FIG. 3A.

Referring back to FIG. 2, optional memory 240 can also be included in relay device 200. Information received from sensor control device 102 and reader device 120 (and any other device) can be stored in memory 240 during the transfer process, or any other relaying procedure. Relay device 200 can store instructions in memory 240 or elsewhere that, when executed, cause one or more processors 230 to take the actions described herein.

Relay device 200 can be powered by a power module 250. Power module 250 can be recharged using charger cord 252 connected from a power source to a charging and/or data jack 260. Charger cord 252 can be a USB cable and jack 260 can be adapted to mate with a desired USB plug configuration. Alternatively, or additionally, relay device 200 can be powered by replaceable or rechargeable batteries 270, for example, coin batteries. Relay device 200 can include a signal (not shown) to indicate relay device 200 is low on power and batteries 270 should be replaced or the device recharged.

Relay device 200 can include clock circuitry 290. In some example embodiments, clock circuitry 290 includes a controllable phase lock loop (PLL). PLL control can be implemented as hardware, such as with circuit 290 or in other embodiments PLL control can be implemented through software (e.g., as instructions executable by a processor of the device) or as a combination of hardware and software.

Figure 3B:
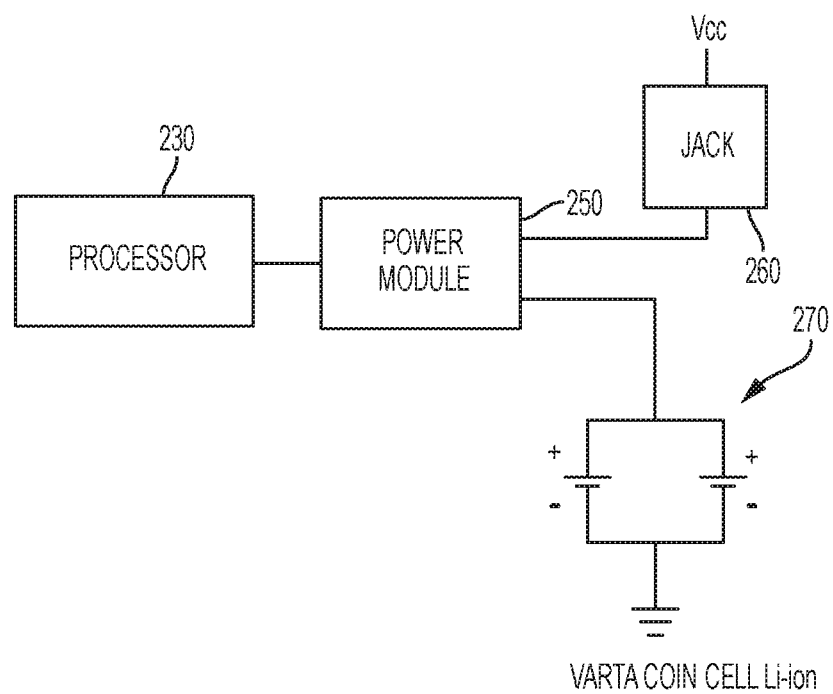

A block diagram of an example power circuit is shown in FIG. 3B. Current can be supplied from batteries 270 to power module 250. Alternatively, current from charger cord 252 can enter jack 260 and flow to power module 250. Power module 250 can disconnect power from the batteries 270 if jack 260 is powered, thereby extending the life of batteries 270. Power module 250 can in turn distribute power to the remaining relay device circuitry 218.

Figure 4A:
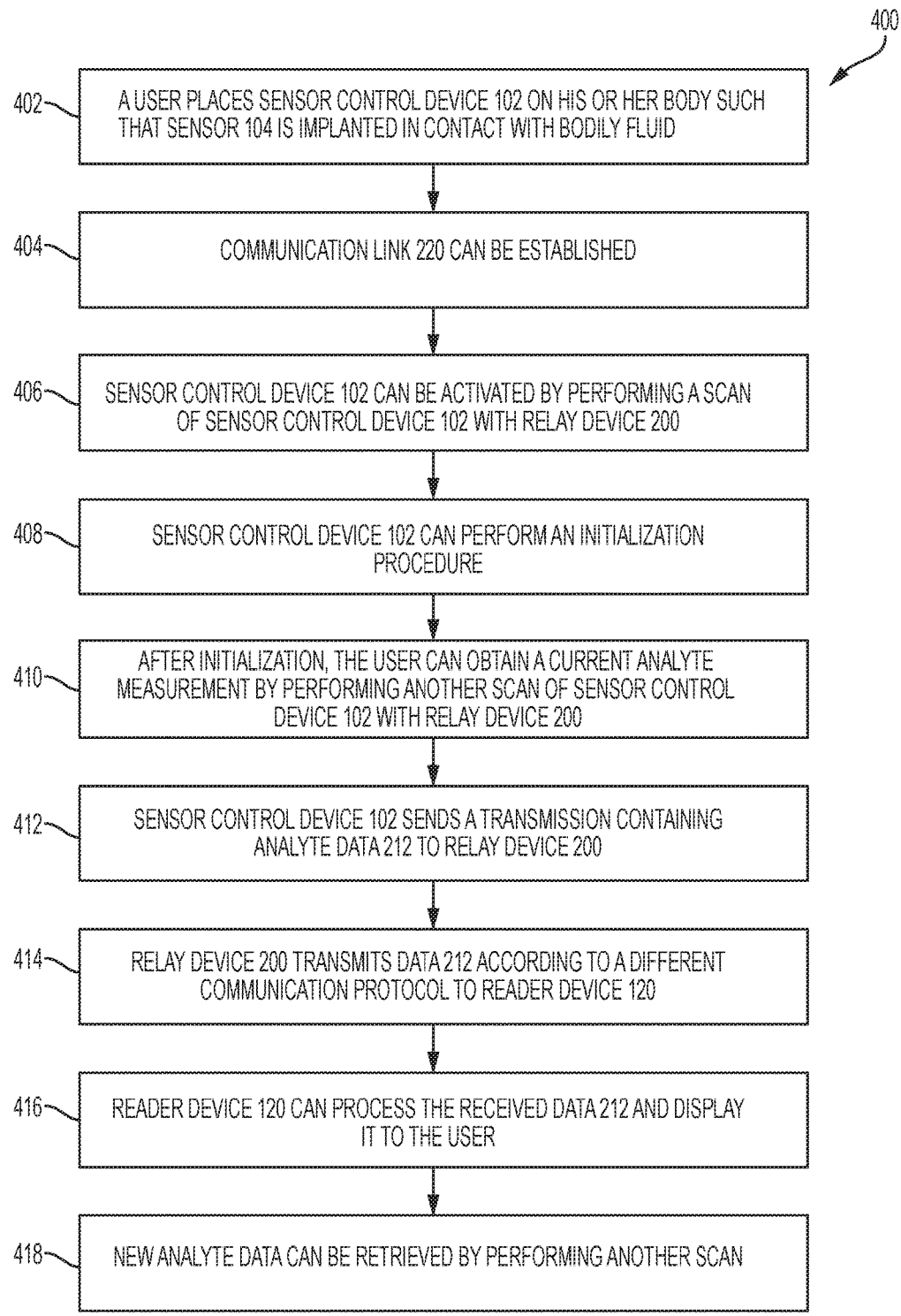
FIG. 4A is a flow diagram depicting an example embodiment of a method of communicating between two devices using a relay device as an intermediary.

FIG. 4A is a flow diagram depicting an example method 400 of using relay device 200 to obtain analyte data in a manner similar to that described with respect to FIG. 2. At 402, a user places sensor control device 102 on his or her body such that sensor 104 is implanted in contact with the user's bodily fluid. This can be performed with an optional insertion device.

At 404, which can take place before or after step 402, communication link 220 can be established. This can be, for example, the pairing of reader device 120 with relay device 200 according to a BT or BTLE protocol. In this embodiment, reader device 120 is a smartphone or other mobile communication device that does not have the requisite capability to communicate with sensor control device 102 over using the sensor's NFC protocol.

Figure 4B:
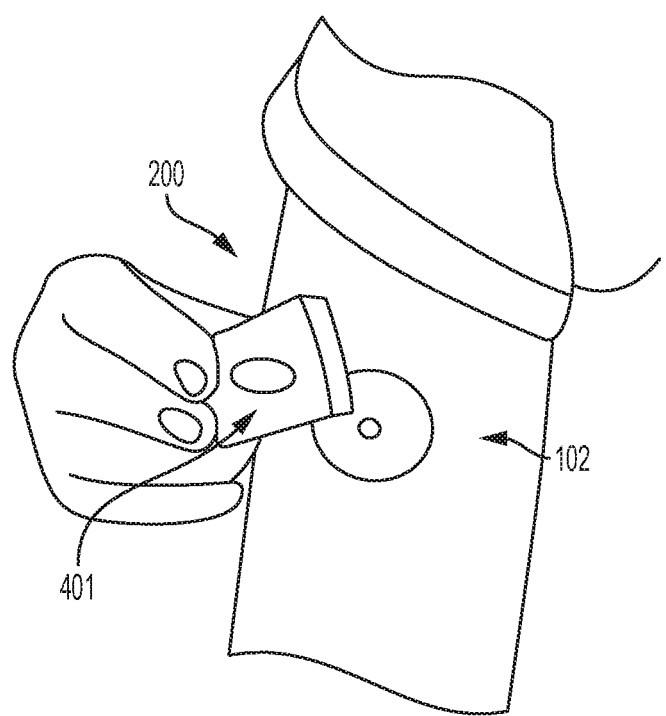
FIG. 4B is an illustration of an example action of scanning a sensor control device with a relay device.

At 406, sensor control device 102 can be activated by performing an NFC scan of sensor control device 102 with relay device 200. The action of scanning sensor control device 102 is depicted in the illustration of FIG. 4B, where relay device 200 is brought into close proximity with sensor control device 102. In some embodiments, relay device 200 is brought within a distance less than twelve inches, or less than ten inches, or less than seven inches, or less than five inches, between the NFC antenna of relay device 200 and the NFC antenna of sensor control device 102 before the NFC scan will occur. Step 406 is preferably performed after implantation of sensor 104 at step 402, but can be performed beforehand as well.

At 408, sensor control device 102 can perform an initialization procedure, also referred to as a warm-up period. In some embodiments, the warm-up period may last for an hour or more. At 410, after the warm-up period completes, the user can obtain a current analyte measurement by performing another scan of sensor control device 102 with relay device 200. This can be accomplished as described with respect to FIG. 2, where reader device 120 sends request 210 to relay device 200 which then relays the request to sensor control device. Or in another embodiment, reader device 120 can be used to instruct relay device 200 to generate its own request 210.

In yet another embodiment, relay device 200 can be used to scan sensor control device 102 without receiving a prior transmission from reader device 120, but instead upon receipt of a user indication. For example, relay device 200 can include a button 401 as shown in FIG. 4B. This user indication can be provided to relay device 200 by depressing button 401 each time the user desires to read analyte data from sensor control device 102.

In still other embodiments, relay device 200 can be programmed to send requests for analyte data according to a schedule. The schedule can be stored in memory of relay device 200 and set by the user and uploaded to relay device 200, or the schedule can be set at the factory prior to distribution to the user. Thus, relay device 200 can repeatedly perform scans without user intervention and also without reliance upon receiving a prior transmission from reader device 120, which might unnecessarily drain the power supply of reader device 120. In some example embodiments, relay device 200 generates a scan request once every 1 to 60 minutes, although generally any desired scan frequency can be programmed.

At 412, sensor control device 102 sends transmission 205 (FIG. 2) containing analyte data 212 to relay device 200, which receives it. At 414, relay device 200 extracts data 212, formats an outgoing transmission 206 containing data 212 and immediately sends the transmission 206 according to a BT or BTLE protocol to reader device 120. At 416, reader device 120 can process the received data 212 and display it to the user. New analyte data can be obtained by the user, at his or her discretion or according to a schedule, by initiating additional scans 418 (similar to that described in step 410).

Button 401 can also function as an on/off button, toggling the relay device 200 between a continuous or on state and an off or low power state; or between a continuous state and an on-demand state. In a continuous state, relay device 200 can scan sensor control device 102 at predetermined time intervals and collect analyte level data as will be described in more detail below. Alternatively, button 401 can function to turn on or awaken relay device 200 from a low power state and initiate an on-demand scan of sensor control device 102. After a predetermined amount of time, relay device 200 can re-enter the off or low power state. In alternate embodiments, button 401 can be used to cycle relay device 200 through several modes, for example, each successive activation of button 401 can cycle relay device 1401 through an on state, low power state, and off state.

Figure 4C:
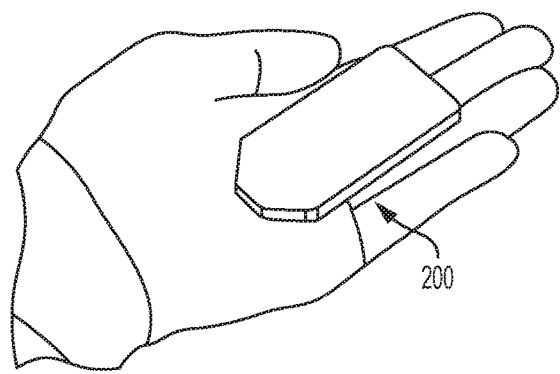
FIGS. 4C-F are illustrations of various structural aspects of example embodiments of relay devices.
Figure 4D:
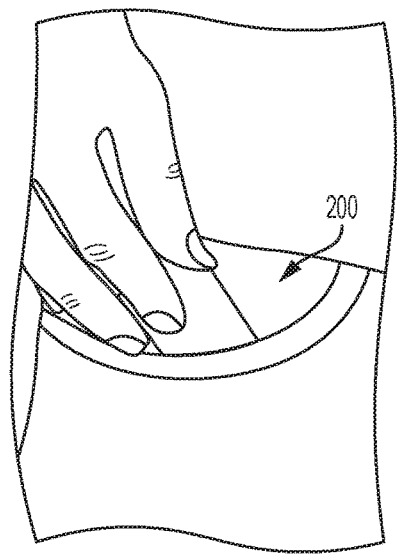
Figure 4E:
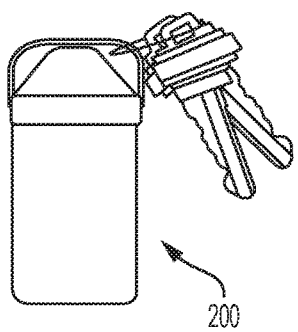
Figure 4F:
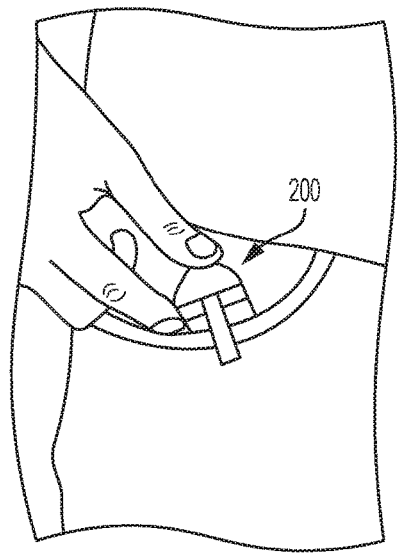

Relay device 200 can be relatively small in size and be implemented in a wide variety of shapes and packages. For example, relay device 200 can be sized to fit in a user's palm (see FIG. 4C) or ordinary pants pocket (see FIG. 4D). Relay device 200 can include an aperture or ring for attachment to a key chain and can be sized similarly to a key fob (see FIG. 4E). Relay device 200 can also or alternatively include a clip for attachment to a pocket (see FIG. 4F), belt, clothing, handbag, backpack, or the like. In these configurations, relay device 200 can maintain a paired connection with a reader device 120, such as a smartphone, also carried on or near the user's body. When a scan of sensor control device 102 is required, relay device 200, can conveniently be moved into close proximity with sensor control device 102.

Figure 4G:
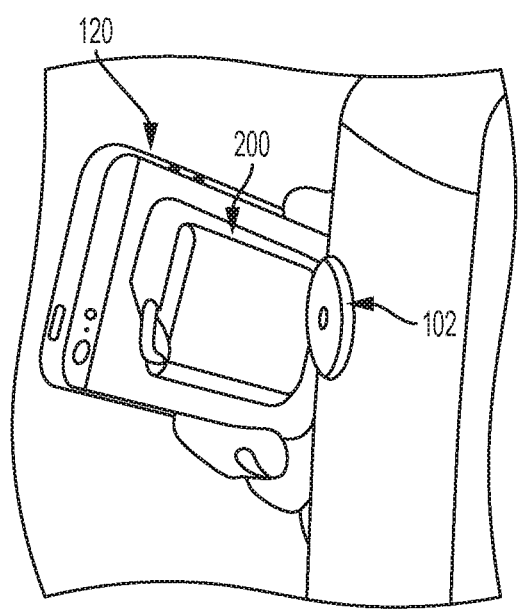
FIG. 4G is an illustration of an example embodiment of a reader device coupled with an example embodiment of a relay device during a scan.

In other embodiments, relay device 200 can be attached to reader device 120, such as with an adhesive backing, a strap, a belt, a clip, and the like. An example embodiment with relay device 200 connected directly to reader device 120 is depicted in FIG. 4G. In these embodiments, reader device 120 with relay device 200 attached thereto can be brought into close proximity with and used to scan sensor control device 102 as a single unit, greatly enhancing the convenience to the user.

Figure 5A:
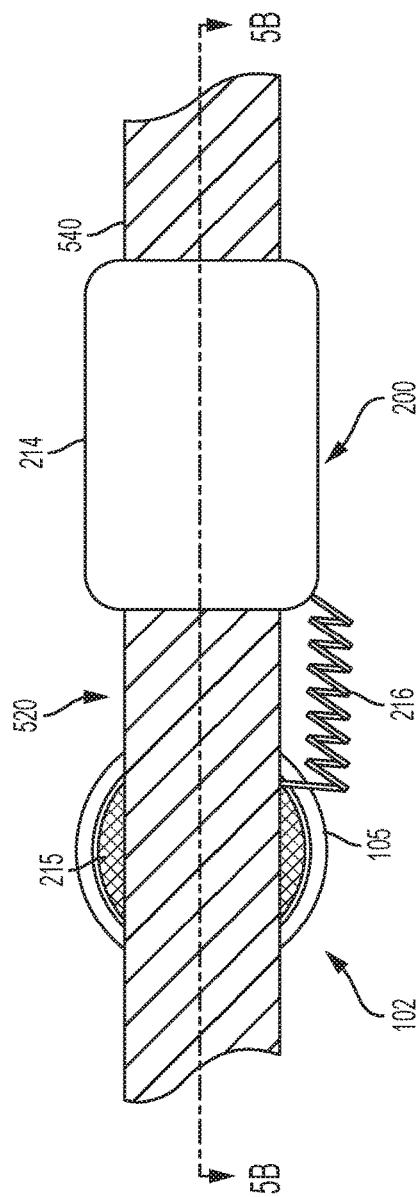
FIG. 5A is a plan view depicting an example embodiment of a relay device in use.
Figure 5B:
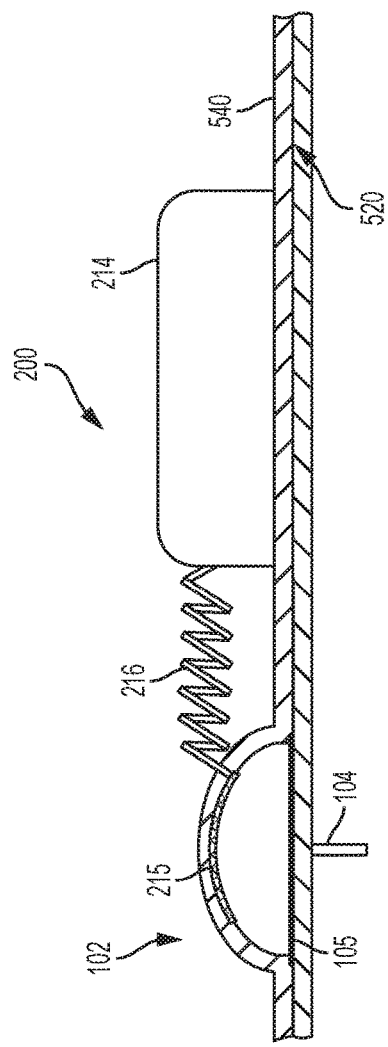
FIG. 5B is an elevational view depicting the relay device taken along 5B-5B in FIG. 5A.

Another example embodiment of relay device 200 is depicted in FIGS. 5A and 5B. In this embodiment, relay device 200 can be worn over sensor control device 102 to read analyte levels and transmit the information to reader device 120, enabling features of in vivo analyte monitoring, such as hypoglycemia and/or hyperglycemia alarms to be generated without having to manually bring reader device 120 (or relay device 200) into close proximity with sensor control device 102. This can have particular advantages while the user is sleeping.

Relay device 200 can be held in place on a user's body or extremity, in proximity to sensor control device 102, by relay device holder 540, such as a sleeve, band, or strap. In the embodiments described herein, relay device holder 540 can be adapted to hold relay device 200 can be held within twelve inches, within ten inches, within seven inches, within five inches, or within one inch of sensor control device 102, or in some embodiments relay device 200 is held in physical contact with sensor control device 102. Relay device holder 540 can be made of elastic or include elastomeric materials or can be made of fabric or cloth that may include elastic or elastomeric materials. Relay device 200 can be held in place by inserting it between the user's body and relay device holder 540, placing it in a pocket attached to relay device holder 540, threading relay device holder 540 through slots, grooves, or openings in housing 214 of relay device 200, or attaching relay device 200 to relay device holder 540 with one or more anchoring devices, such as snaps, clips, buckles, or a hook and loop fastener such as a VELCRO fastener, or any combination thereof.

FIG. 5A is a top view depicting an example embodiment of relay device 200 and relay device holder 540 while in use and FIG. 5B is a cross-sectional view taken along line 5B-5B of FIG. 5A. Sensor control device 102 is shown attached with adhesive patch 105 to the surface of the user's skin 520 with analyte sensor 104 inserted into the user's body (see FIG. 5B). Antenna 215 of relay device 200 is placed over sensor control device 102 and is held in place by relay device holder 540. Alternatively, antenna 215 can be clipped, threaded, or snapped onto sensor control device 102, in which case relay device holder 540 can be adjacent to sensor control device 102 instead of being over the same. Housing 214 of relay device 200 can be attached to relay device holder 540 at a location near sensor control device 102 such that wire cable 216 connecting antenna 215 and housing 214 is not stressed and allows some movement without pulling on sensor control device 102 and potentially causing unintended removal or user pain. In this particular example embodiment, wire cable 216 is coiled to facilitate stretching, however other wire cables can be used, stress-free or low-stress or otherwise.

The relay device 200 shown in FIGS. 5A and 5B can be worn by a user during sleep allowing data from sensor control device 102 to be sent wirelessly (by radio frequency (RF)) in real time, or near real time, to reader device 120, such as a smartphone, capable of providing alarms or other feedback to the user. Data can be stored in memory 240 of relay device 200, or can be sent from relay device 200 upon receipt from sensor control device 102 without being stored in memory 240. When continuous monitoring of analyte levels is no longer desired, the user can remove relay device 200 and place sensor control device 102 into an on-demand mode, if the sensor control device 102 is adapted for mode switching. In some embodiments, once activated, sensor control device 102 remains in the same communication mode, for example, the on-demand mode where sensor control device 102 repeatedly measures analyte levels but only communicates them when queried by reader device 120 or relay device 200, or the continuous mode where sensor control device 102 again repeatedly measures analyte levels but communicates them according to a schedule or at certain intervals without necessarily being queried first by reader device 120 or relay device 200. Relay device 200 can be installed, removed, and installed again over the same sensor control device 102 as many times as desired to enable data collection.

Figure 6:
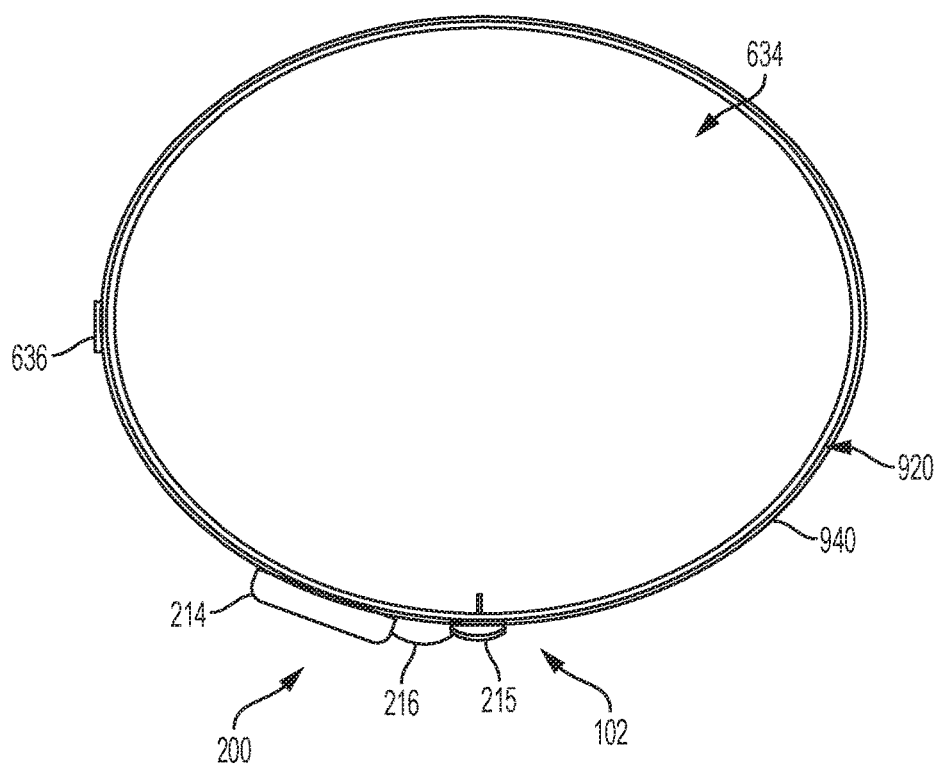
FIG. 6 is a cross-sectional view depicting the relay device of FIGS. 5A and 5B being worn by a user.

FIG. 6 shows relay device 200 attached to a part of a user's body 634 with relay device holder 540. Relay device 200 can be attached, for example, to the user's arm, abdomen, or any other part of the user's body 634 where sensor control device 102 is implanted. As shown in FIG. 6, relay device holder 540 can wrap around the part of the user's body 634 and the ends of holder 540 can be coupled together with fastener 636. As in attaching relay device 200 to holder 540, fastener 636 can be one or more snaps, clips, buckles, hook and loop fasteners such as VELCRO fasteners, or any combination thereof. While FIG. 6 shows relay device holder 540 between housing 214 of relay device 200 and the part of the user's body 634, in alternative embodiments, relay device housing 214, wire cable 216, and/or antenna 215 can be positioned between relay device holder 540 and the part of the user's body 634.

Figure 7:
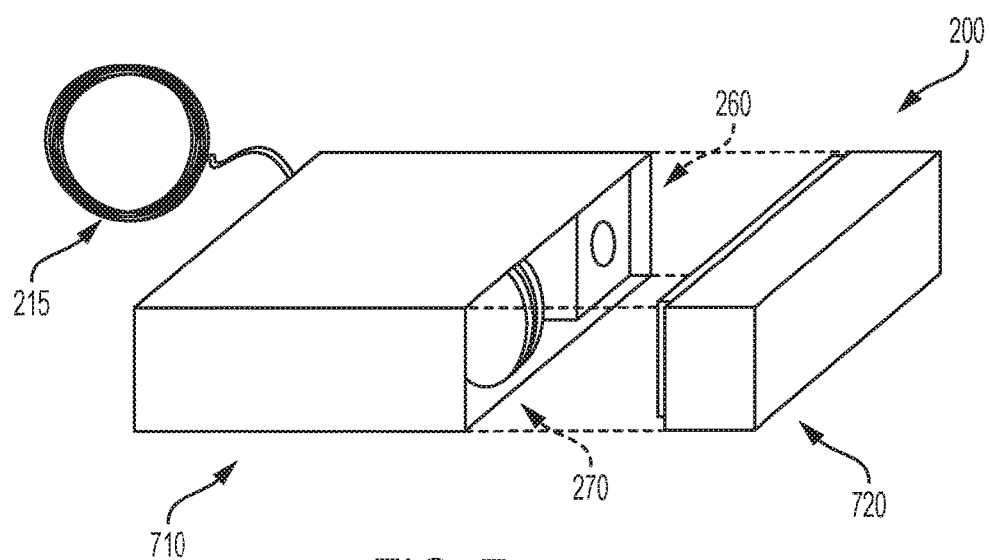
FIG. 7 is a perspective view depicting another example embodiment of a relay device.

As shown in FIG. 7, relay device 200 can be enclosed in a modular housing having a main section 710 that includes electronic circuitry 218 (not shown) and cap 720 that can be secured to the main section in a water-tight fashion. Cap 720 can be removed to allow the user to access batteries 270 and charging jack 260. Cap 720 can be separate from the main section as shown, or cap 720 can be attached along an edge or with a tether to avoid being lost. Additionally, cap 720 can be held securely in place with screws, or other fastening devices, to avoid unintentionally being removed.

Relay device 200 can be implemented without a graphical display (e.g., a touchscreen) to increase battery life and lower cost. Relay device 200 takes advantage of wireless communication devices 120, for example BT-enabled smartphones, that can execute an app to display the status of relay device 200, configure it, and provide alarms. However, it is possible to provide relay device 200 with a user interface electrically connected to the processing circuitry of relay device 200 so that reader device 120 is not needed. To the extent communication is desired between a user and relay device 200, user input can be provided to relay device 200 by one or more inputs such as depressible buttons, switches, a roller wheel, or the like. Indications (e.g., power on, power off, a scan is successful, a scan has failed, etc.) can be communicated from relay device 200 to the user by the way of one or more lights (e.g., a light emitting diode (LED))

and/or one or more audible sounds (e.g., a beep or a tone from a speaker, etc.) without using a touchscreen or other graphical display.

Reader device 120, or relay device 200 if properly equipped, can provide alarms for several conditions, including low battery, hyperglycemia, hypoglycemia, rapid analyte level rise or fall, and reader device 120 being out-of-range of relay device 200. When configured to provide low battery alarms, such can be activated when either sensor control device 102 or relay device 200 nears a state where the respective device will have insufficient power for operation. An alarm can be triggered well in advance of this state, allowing the user time to recharge or replace relay batteries 270, or replace sensor control device 102.

In some embodiments, reader device 120 polls relay device 200 periodically and compares the acquired analyte values with one or more alarm thresholds. If analyte levels are found to be outside established thresholds, an alarm is triggered. In some other embodiments, relay device 200 can be configured to compare analyte readings with one or more alarm thresholds and when an alarm condition occurs, transfer analyte data to reader device 120 along with triggering an alarm. Automatic transfer of analyte data from relay device 200 to reader device 120 only under alarm conditions may reduce power requirements of one or both devices 120 and 200, since wireless communication need occur only when an alarm condition is detected. The user can still manually request transfer and display of recent analyte data on demand. In yet other embodiments, with relay device 200 configured to monitor alarm conditions, reader device 120 can be configured to poll relay device 200 at a longer period of time. Thus, if an alarm condition occurs, relay device 200 can transfer data to reader device 120 and trigger an alarm. However, in the absence of an alarm condition, relay device 200 can be configured to periodically transfer data.

In some embodiments, out-of-range alarms can be set. If a user is relying on the system to provide an analyte alarm, an out-of-range situation where relay device 200 and reader device 120 are not within communication range of one another could mean that an alarm condition is missed. To mitigate this, reader device 120 can detect that it is out-of-range of relay device 200 (for instance, if it did not get a response from a periodic communication poll) and set off an out-of-range alarm. In other embodiments, relay device 200 can include an enunciator, such as an audio beeper or a vibrator. Relay device 200 can be configured to enunciate when a predetermined period of time has elapsed since reader device 120 last responded to a communication from relay device 200.

As previously described, one example application for relay device 200 is to monitor analyte levels while the user is sleeping and through the use of alarms, notify the user of any conditions that need acting upon. Another application for relay device 200 is data logging of measured readings transmitted from sensor control device 102. Relay device 200 can read and store sensor control device data for up to the full duration of time that relay device 200 is worn. Data can be relayed wirelessly to reader device 120, drug delivery device 160, or computer system 170. While relay device 200 is being worn and in use, sensor control device 102, in a continuous mode, can still be read by reader device 120 on demand.

During use, the read frequency at which relay device 200 reads data from sensor control device 102 can be adjusted for battery life or other considerations. In some embodiments, relay device 200 can send a query for analyte data to sensor control device 102 at regular intervals, for example, every 1 to 10 minutes, although longer or shorter intervals can be used as well. Data transfer between relay device 200 and reader device 120 can also occur at regular intervals, for example, every 1 to 60 minutes, although longer or shorter intervals can be used as well. Data transfer from relay device 200 to reader device 120 can also occur immediately upon the detection of an alarm condition if relay device 200 is monitoring received sensor data for data excursions.

Another consideration for the read frequency is data integrity. To illustrate, in an example embodiment of system 100 in which sensor control device 102 obtains an analyte reading every one minute, relay device 200 can be configured to read data from sensor control device 102 no faster than once every three minutes. In some embodiments, the loss of one point of data every three minutes may be tolerated without significant degradation of clinical efficacy, but in other embodiments, it may be desirable to rectify that loss or more significant losses.

In some embodiments, antenna 215 of relay device 200 may generate a relatively high energy magnetic field. If such a high energy field is generated during a scan then this may corrupt analog to digital conversions that are in process in sensor control device 102 (e.g., within an analog to digital converter of AFE 852 (described with respect to FIG. 11 herein). If a scan occurs during the analog to digital conversion, sensor control device 102 can flag the potentially corrupted measurement as invalid and the data point may be deleted or ignored in the algorithmic processing of sensor control device 102, reader device 120, or other device. This algorithmic processing can be of the type that converts raw sensor data (e.g., analog or digital electrical measurements, temperature data, etc.) into a user readable form. The user readable form can be a textual or numeric value, or graphical indication, that can be interpreted by an ordinary user as representative of that user's analyte level (e.g., glucose in milligrams per deciliter (mg/dL) or millimoles per liter (mmol/L)).

Alternatively, the rate at which relay device 200 obtains data from sensor control device 102 can be synchronized with the rate at which sensor control device 102 determines analyte levels. Using the same example embodiment, in the 1 minute cycle of the sensor control device, the analog to digital converter may be active for approximately 40 seconds. During the remaining 20 seconds of the cycle, the analog subsystem is idle so a scan during this period will not corrupt the analog conversion. Synchronizing relay device 200 to read data during the 20 second idle period results in none of the transferred data being flagged as corrupt. The fraction of a cycle that the analog to digital converter is active depends, among other things, on the conversion speed of the analog to digital converter. These time values are for example only and are not limiting. Furthermore, the synchronization embodiments described herein can be used to align scan requests with any suitable time period, not limited to only those time periods in which sensor control device 102 or a particular component thereof is "idle."

In many embodiments, sensor control device 102 includes an electrical clock circuit (such as clock circuit 290 described with respect to FIG. 2) that can be used for scheduling software activities. This clock circuit can be used to synchronize relay device 200 with sensor control device 102. The phase of sensor control device 102 can be the clock's time mod cycle time (e.g., in seconds). Thus, in this example, the phase of sensor control device 102 is the clock's time mod 60, or $0 \leq phase < 60$. During the first 40 seconds of the cycle, $0 \leq phase < 40$, if a scan of sensor control device 102 by relay device 200 occurs, then sensor control device 102 can flag or otherwise treat the measurement data as being invalid, for example, by associating a bit or sequence of bits with the data that flags that data to subsequent devices (e.g., 120 or 200) as being invalid or possibly corrupt, or by deleting the data altogether. During the final 20 seconds of the cycle, 40≤phase<60, if a scan occurs, then the measurement is not flagged as invalid, or alternatively is flagged in a similar fashion as being valid.

A timing indication, such as the phase value or otherwise, can be included in the sensor control device's data payload transmitted to relay device 200 (or reader device 120). It may be included in a portion of the payload that has a checksum, or it may be included in a portion that does not have a checksum. Check summing the phase will take processor time during the scan so the decision to include a checksum can depend on the processor capabilities of the sensor control device 102.

Relay device 200 can use the timing indication from each scan to schedule the next scan during sensor control device 102 idle time. Sensor control device 102 generally cycles from active time to idle time and back to active time, and so forth. Relay device 200 can have information about the sensor control device's cycle stored in memory, or that information can be transmitted to relay device 200 by sensor control device 102. That information can include the relative relationship between the duration of the active time (e.g., the time during which a measurement is made and processed by sensor control device, or the time during which analog to digital converter of sensor control device is actively converting analog analyte data to digital form) and the idle time (e.g., the time during which no measurement is made nor processed by sensor control device, or the time during which analog to digital converter of sensor control device is not actively converting analog analyte data to digital form) of sensor control device. This relative relationship, which may be expressed as relative lengths of time or relative amounts of a time period, can be used by relay device 200 with the timing indication to determine an appropriate time to transmit a request for analyte data to sensor control device 102.

Continuing with the example, if the timing indication is the phase of sensor control device 102, and that phase when scanned is 30, then relay device 200 can postpone the next scan by a time between 10 and 30 seconds in order to scan sensor control device 102 when the phase is between 40 and 60, i.e., during the idle time of this example. In one example embodiment, relay device 200 can postpone the next scan by 20 seconds in order to scan sensor control device 102 when the phase is 50, i.e., the middle of the idle period. However, a scan may be executed at any time in the idle period, without having the data tagged as invalid.

Furthermore, in many embodiments relay device 200 will not transmit a scan request during each idle time of sensor control device 102, but rather only when a request is first received from reader device 120, or when a user indication for a scan request is input to relay device 200 (such as through a button or other user interface on device 200), or according to a programmed schedule stored within relay device 200. In those and other embodiments, relay device 200 can use the aforementioned synchronization process to delay the subsequent scan request that is to be transmitted from relay device 200 to sensor control device 102 until sensor control device 102 enters an idle time period.

However, the sensor control device's clock can be subject to phase drift. For example, the clock in sensor control device 102 may have a time base error of ±3 seconds. Over a 15 minute time period, the error can be as large as ±27 seconds, causing the phase to drift. To ensure that the scan occurs within the idle period, relay device 200 can include phase lock loop (PLL) control, such as in clock circuit 290 (FIG. 2).

There are many forms of PLL control, trading off complexity, lock time, phase error, etc. In this example, the PLL control has the ability to maintain phase lock when one or more scans are not successful. An example of PLL control logic for relay device 200 is:

*a*) difference=(ReportedPhase−DesiredPhase)

*b*) ratio=LastDelta/SensorDelta

*c*) NextDelta=(DesiredInterval−difference)*ratio where: SensorDelta=ReportedPhase−PreviousPhase+ DesiredInterval;

DesiredPhase is the desired phase for the scan and ReportedPhase is the actual phase when the scan was taken; and DesiredInterval is the desired time between subsequent scans.

The next scan is scheduled NextDelta seconds in the future, and then before the next scan setting:
LastDelta=NextDelta
PreviousPhase=ReportedPhase Each time a scan is completed, relay device 200 executes the PLL control logic to determine the next scan time, thereby maintaining phase lock with sensor control device 102. Other forms of PLL are possible and may be employed.

These embodiments describing synchronization of transmissions between relay device 200 (or another device) and sensor control device 102 provide solutions to problems that necessarily arise from the use of electronic devices to, e.g., monitor an analyte level. For example, because the sensor control device 102 includes analog to digital circuitry (or other circuitry) the operation of which can be interfered with by the presence of a relatively strong wireless transmission, such as that which can be generated by an NFC transmission, the problem as well as the solutions thereto are rooted in the technology of these systems. For this reason, as well as others, these embodiments are not abstract.

Figure 8:
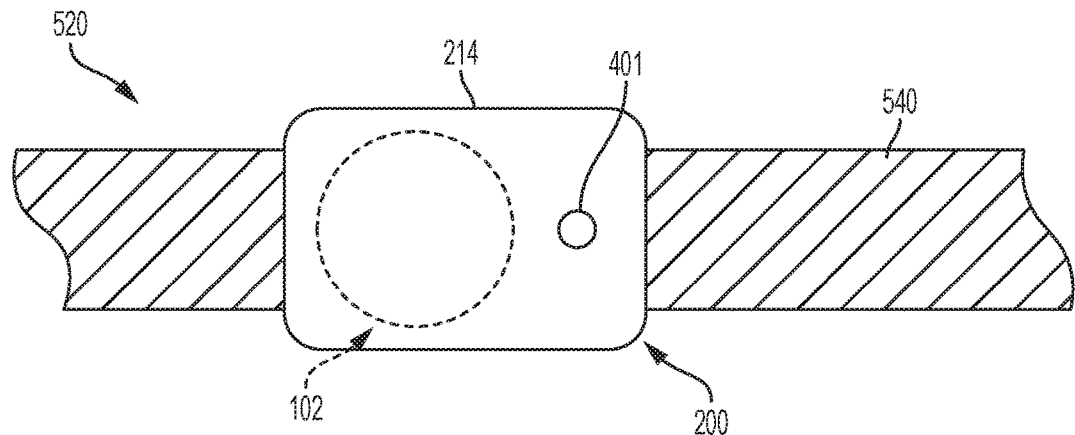
FIGS. 8-9 are plan views depicting additional example embodiments of a relay device in use.

FIG. 8 depicts relay device 200 in use with relay device holder 540, similar to relay device 200 in FIGS. 5A and 5B. In this example embodiment, relay device 200 can be held in place over sensor control device 102 (dashed line) with relay device holder 540. Relay device 200 can be positioned such that internal antenna 215 (not shown) is in proximity to sensor control device 102. Relay device 200 can be placed into a continuous, or frequently repeating mode for monitoring of analyte levels, for example, monitoring of analyte levels while the user is asleep. In alternative example embodiments, relay device 200 can be used in an on-demand mode in which analyte level data is obtained from sensor control device upon activation of button 401.

Figure 9:
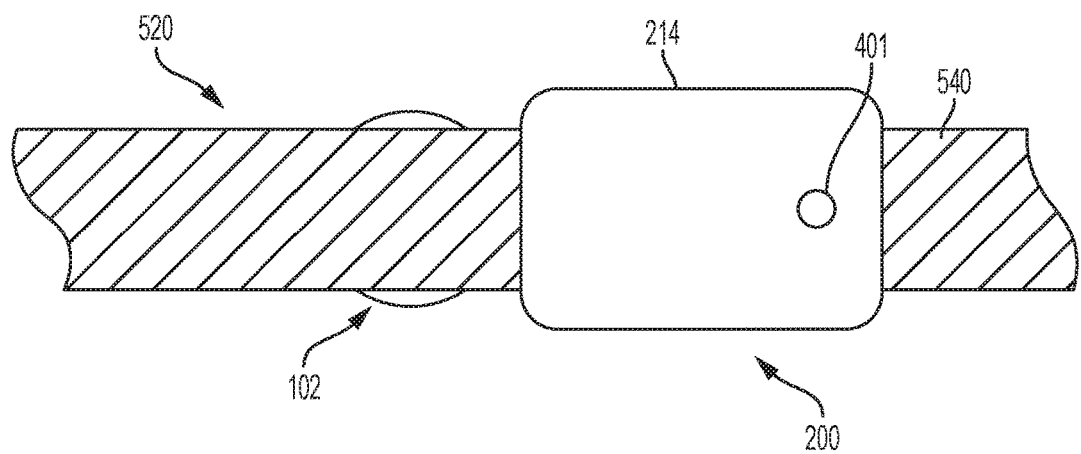

FIG. 9 depicts shows relay device 200 in use with relay device holder 540 in an alternative embodiment. In this example embodiment, relay device 200 can be held in place with relay device holder 540. Relay device 200 can be positioned near, for example, several inches or less from, sensor control device 102 such that internal antenna 215 (not shown) is in proximity to sensor control device 102. Relay device 200 can be placed into continuous mode for monitoring of analyte levels, for example, monitoring of analyte levels while the user is asleep. In alternative example embodiments, relay device 200 can be used in an on-demand mode in which analyte level data is obtained from sensor control device upon activation of button 401.

Additional detail is now provided with respect to reader device 120 and sensor control device 102. As discussed above, reader device 120 can be a mobile communication device such as, for example, a Wi-Fi or internet enabled smartphone, tablet, or personal digital assistant (PDA). Examples of smartphones can include, but are not limited to, those phones based on a WINDOWS operating system, ANDROID operating system, IPHONE operating system, PALM WEBOS, BLACKBERRY operating system, or SYMBIAN operating system, with network connectivity for data communication over the internet or a local area network (LAN).

Reader device 120 can also be configured as a mobile smart wearable electronics assembly, such as an optical assembly that is worn over or adjacent to the user's eye (e.g., a smart glass or smart glasses, such as GOOGLE GLASSES). This optical assembly can have a transparent display that displays information about the user's analyte level (as described herein) to the user while at the same time allowing the user to see through the display such that the user's overall vision is minimally obstructed. The optical assembly may be capable of wireless communications similar to a smartphone. Other examples of wearable electronics include devices that are worn around or in the proximity of the user's wrist (e.g., a watch, etc.), neck (e.g., a necklace, etc.), head (e.g., a headband, hat, etc.), chest, or the like.

Figure 10:
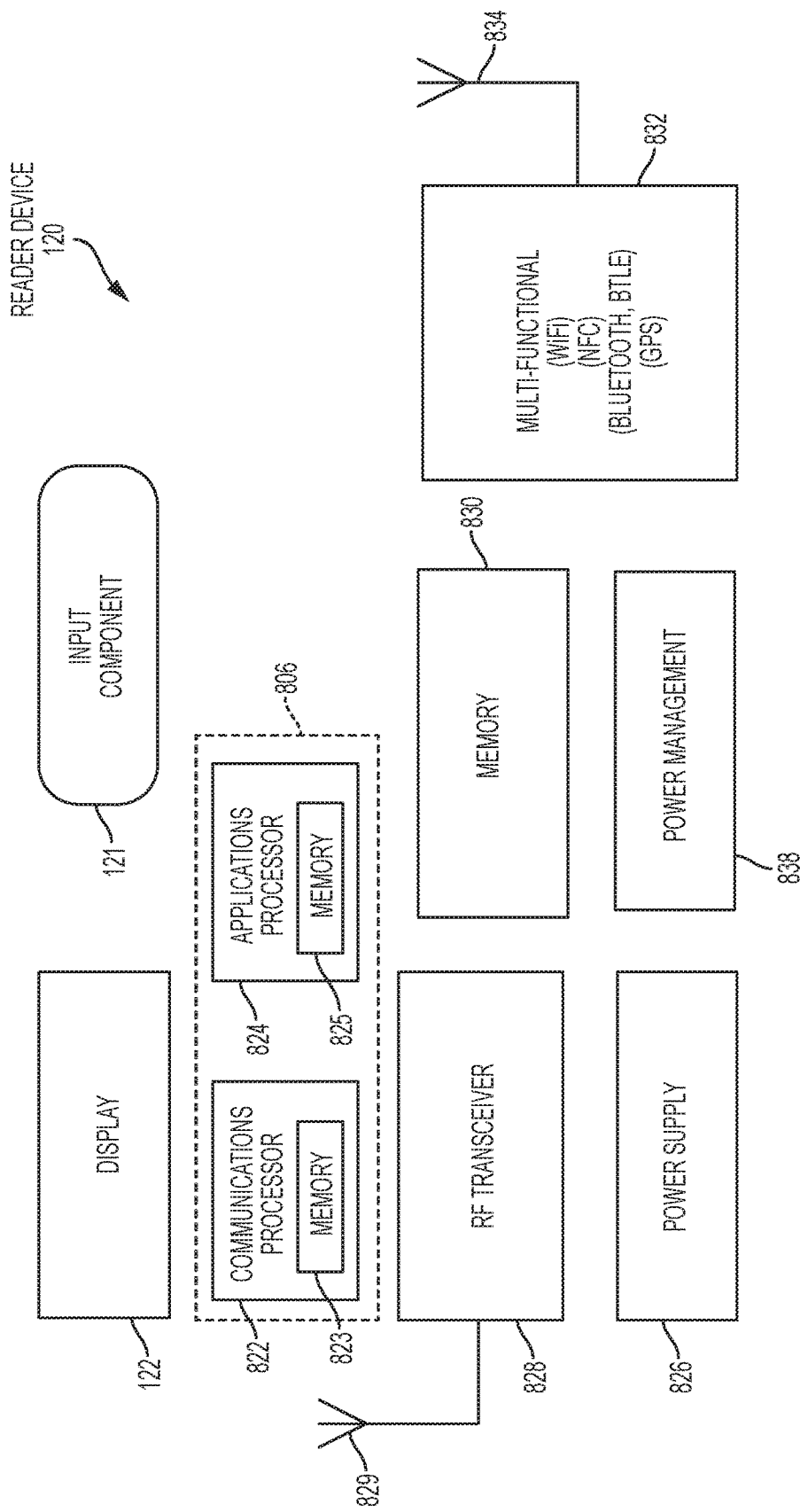
FIG. 10 is a block diagram depicting an example embodiment of a reader device configured as a smartphone.

FIG. 10 is a block diagram of an example embodiment of a reader device 120 in the form of a smartphone. Here, reader device 120 includes an input component 121, display 122, and processing hardware 806, which can include one or more processors, microprocessors, controllers, and/or microcontrollers, each of which can be a discrete chip or distributed amongst (and a portion of) a number of different chips. Here, processing hardware 806 includes a communications processor 822 having on-board non-transitory memory 823 and an applications processor 824 having on-board non-transitory memory 825. Reader device 120 further includes an RF transceiver 828 coupled with an RF antenna 829, a memory 830, multi-functional circuitry 832 with one or more associated antennas 834, a power supply 826, and power management circuitry 838. FIG. 10 is an abbreviated representation of the internal components of a smartphone, and other hardware and functionality (e.g., codecs, drivers, glue logic, etc.) can of course be included.

Communications processor 822 can interface with RF transceiver 828 and perform analog-to-digital conversions, encoding and decoding, digital signal processing and other functions that facilitate the conversion of voice, video, and data signals into a format (e.g., in-phase and quadrature) suitable for provision to RF transceiver 828, which can then transmit the signals wirelessly. Communications processor 822 can also interface with RF transceiver 828 to perform the reverse functions necessary to receive a wireless transmission and convert it into digital data, voice, and video.

Applications processor 824 can be adapted to execute the operating system and any software applications that reside on reader device 120 (such as any sensor interface application or analyte monitoring application that includes, e.g., SLL 304), process video and graphics, and perform those other functions not related to the processing of communications transmitted and received over RF antenna 829. Any number of applications can be running on reader device 120 at any one time, and will typically include one or more applications that are related to a diabetes monitoring regime, in addition to the other commonly used applications that are unrelated to such a regime, e.g., email, calendar, weather, etc.

Memory 830 can be shared by one or more the various functional units present within reader device 120, or can be distributed amongst two or more of them (e.g., as separate memories present within different chips). Memory 830 can also be a separate chip of its own. Memory 830 is non-transitory, and can be volatile (e.g., RAM, etc.) and/or non-volatile memory (e.g., ROM, flash memory, F-RAM, etc.).

Multi-functional circuitry 832 can be implemented as one or more chips and/or components, including communication circuitry, that perform other functions such as local wireless communications (e.g., Wi-Fi, Bluetooth, Bluetooth Low Energy) and determining the geographic position of reader device 120 (e.g., global positioning system (GPS) hardware). One or more other antennas 834 are associated with both the functional circuitry 832 as needed.

Power supply 826 can include one or more batteries, which can be rechargeable or single-use disposable batteries. Power management circuitry 838 can regulate battery charging and power supply monitoring, boost power, perform DC conversions, and the like. As mentioned, reader device 120 may also include one or more data communication ports such as USB port (or connector) or RS-232 port (or any other wired communication ports) for data communication with a remote terminal 170, or sensor control device 102, to name a few.

Figure 11:
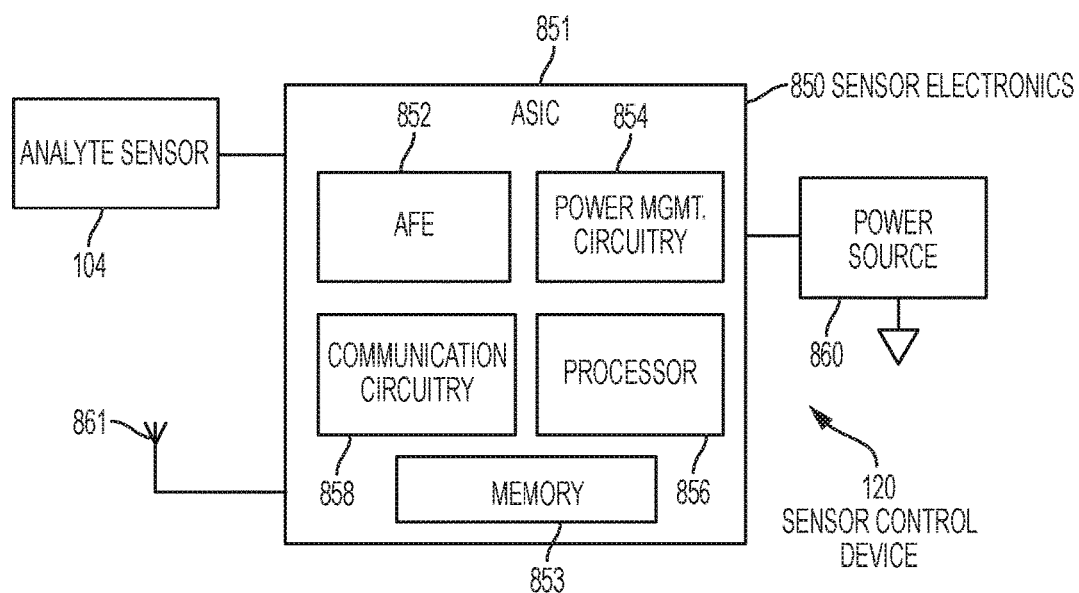
FIG. 11 is a block diagram depicting an example embodiment of a sensor control device.

FIG. 11 is a block schematic diagram depicting an example embodiment of sensor control device 102 having analyte sensor 104 and sensor electronics 850 (including analyte monitoring circuitry). Although any number of chips can be used, here the majority of the sensor electronics 850 are incorporated on a single semiconductor chip 851 that can be, e.g., a custom application specific integrated circuit (ASIC). Shown within ASIC 851 are several high-level functional units, including an analog front end (AFE) 852, power management circuitry 854, processor 856, and communication circuitry 858 (which can be implemented as a transmitter, receiver, transceiver, passive circuit, or otherwise according to the communication protocol). In this embodiment, both AFE 852 and processor 856 are used as analyte monitoring circuitry, but in other embodiments either circuit can perform the analyte monitoring function. Processor 856 can include one or more processors, microprocessors, controllers, and/or microcontrollers.

A non-transitory memory 853 is also included within ASIC 851 and can be shared by the various functional units present within ASIC 851, or can be distributed amongst two or more of them. Memory 853 can be volatile and/or non-volatile memory. In this embodiment, ASIC 851 is coupled with power source 860, which can be a coin cell battery, or the like. AFE 852 can include an analog-to-digital converter and interfaces with in vivo analyte sensor 104 and receives measurement data therefrom and outputs the data to processor 856 in digital form, which in turn processes the data to arrive at the end-result analyte discrete and trend values, etc. This data can then be provided to communication circuitry 858 for sending, by way of antenna 861, to reader device 120 (not shown) where further processing can be performed by, e.g., the sensor interface application. It should be noted that the functional components of ASIC 851 can also be distributed amongst two or more discrete semiconductor chips.

Performance of the data processing functions within the electronics of the sensor control device 102 provides the flexibility for system 100 to schedule communication from sensor control device 102 to reader device 120, which in turn limits the number of unnecessary communications and can provide further power savings at sensor control device 102.

Information may be communicated from sensor control device 102 via relay device 200 to reader device 120 automatically and/or continuously when the analyte information is available, or may not be communicated automatically and/or continuously, but rather stored or logged in a memory of sensor control device 102, e.g., for later output.

For example, in some embodiments reader device 120 and/or relay device 200 can be an "on-demand" reader that requests a reading from sensor control device 102 upon actuation by the user. Relay device 200 can be configured to obtain readings from sensor control device 102 at fixed intervals in a continuous or repeating mode. When relay device 200 is used in addition to reader device 120, sensor control device 102 can provide both continuous readings to relay device 200 and on-demand readings to reader device 120. Any communication protocol used by reader device 120 to communicate with sensor control device 102 can also be used by relay device 200.

Relay device 200 can communicate with a commercially available reader device 120, such as a smartphone, that can perform functions associated with reader device 120. For example, in some embodiments, reader device 120 can communicate with sensor control device 102, directly or indirectly through relay device 200, or computer system 170 using wired or wireless protocols, and can process data received from relay device 200. Additionally, reader device 120 can provide an alarm to notify the user of analyte levels that are outside predetermined ranges. Alarm can be visual (for example, the display of the smartphone can flash), auditory (for example, an alarm tone can be played), and/or tactile (for example, the smartphone can vibrate) and can remain activated until the user responds to alarm.

For each and every embodiment of a method disclosed herein, systems and devices capable of performing each of those embodiments are covered within the scope of the present disclosure. For example, embodiments of relay devices are disclosed and these devices can have one or more memories for storing one or more instructions that, when executed, cause one or more processor to execute or cause the execution of (e.g., via the issuance of an instruction to another responsible circuit) any and all method steps. These relay device embodiments can be used and can be capable of use to implement those steps performed by a relay device from any and all of the methods described herein. The same holds true for those other devices described herein, such as sensor control devices and reader devices.

Likewise, embodiments of relay devices and reader devices are disclosed having one or more transmitters, receivers, memories, power sources, processors and/or controllers that can be programmed to execute any and all method steps or facilitate the execution of any and all method steps. These embodiments of the reader devices can be used to implement those steps performed by a reader device from any and all of the methods described herein. Embodiments of computer systems are also disclosed. These computer systems can include one or more processors, controllers, transmitters, receivers, memories, databases, servers, and/or networks, and can be discretely located or distributed across multiple geographic locales.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

As used herein and in the appended claims, the singular forms "a", "an", and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An in vivo analyte monitoring system, comprising:
   (a) a sensor control device comprising:
      an analyte sensor adapted to sense an analyte level in a human body; and
      wireless communication circuitry adapted to wirelessly transmit data indicative of the sensed analyte level according to a near field communication (NFC) protocol;
   (b) a relay device comprising:
      first wireless communication circuitry adapted to receive the data indicative of the sensed analyte level directly from the sensor control device according to the NFC protocol, wherein the first wireless communication circuitry is configured to transmit a request for analyte data to the sensor control device;

second wireless communication circuitry adapted to wirelessly transmit the data indicative of the sensed analyte level according to a Bluetooth or Bluetooth Low Energy protocol;

processing circuitry; and a memory on which one or more instructions are stored that, when executed by the processing circuitry, cause the processing circuitry to cause the first wireless communication circuitry to transmit the request for analyte data to the sensor control device during an idle time of the sensor control device; and (c) a handheld reader device comprising:

wireless communication circuitry adapted to receive the data indicative of the sensed analyte level directly from the relay device according to the Bluetooth protocol;

processing circuitry; and a memory on which one or more instructions are stored that, when executed by the processing circuitry, cause the processing circuitry to convert the data indicative of the sensed analyte level into a user readable form.

2. The system of claim 1, wherein the one or more instructions stored on the memory of the relay device, when executed by the processing circuitry, cause the processing circuitry to transfer the received data indicative of the sensed analyte level from the first wireless communication circuitry to the second wireless communication circuitry.

3. The system of claim 2, wherein the one or more instructions stored on the memory of the relay device, when executed by the processing circuitry, cause the processing circuitry to transfer the received data indicative of the sensed analyte level, without modifying analyte level information conveyed by the received data, from the first wireless communication circuitry to the second wireless communication circuitry.

4. The system of claim 1, wherein the relay device is adapted to operate without a graphical display.

5. The system of claim 1, wherein the one or more instructions stored on the memory of the relay device, when executed by the processing circuitry, cause the processing circuitry to:

read a timing indication received from the sensor control device; and determine, based at least in part on the timing indication, a time at which transmission of the request for analyte data to the sensor control device will be during an idle time of the sensor control device.

6. The system of claim 5, wherein the idle time of the sensor control device is a time during which an analog to digital converter of the sensor control device is not converting sensed analog analyte data to digital form.

7. The system of claim 5, wherein the timing indication is a phase of a clock of the sensor control device.

8. The system of claim 5, wherein the sensor control device further comprises:

processing circuitry; and a memory on which one or more instructions are stored that, when executed by the processing circuitry, cause the processing circuitry to flag measurement data collected from the analyte sensor if the request for analyte data was received from the relay device during an active time of the sensor control device.

9. The system of claim 8, wherein the active time is a time during which the measurement data was collected by the analyte sensor or a time during which the measurement data collected by the analyte sensor was converted from analog to digital form.

10. The system of claim 8, wherein the one or more instructions stored on the memory of the sensor control device, when executed by the processing circuitry of the sensor control device, cause the wireless communication circuitry to transmit the data indicative of the sensed analyte level including flagged measurement data.

11. The system of claim 10, wherein the one or more instructions stored on the memory of the handheld reader device, when executed by the processing circuitry of the reader device, cause the processing circuitry to convert the data indicative of the sensed analyte level into the user readable form while ignoring flagged measurement data.

12. The system of claim 1, wherein the handheld reader device is a smartphone.

* * * * *